US008053565B2

(12) United States Patent
Snyder

(10) Patent No.: US 8,053,565 B2
(45) Date of Patent: Nov. 8, 2011

(54) MULTI-MEDIA AFFINITY COLUMN TO PREVENT LEACHING OF LIGANDS

(75) Inventor: Mark A. Snyder, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 246 days.

(21) Appl. No.: 12/473,958

(22) Filed: May 28, 2009

(65) Prior Publication Data

US 2010/0305310 A1    Dec. 2, 2010

(51) Int. Cl.
*C07K 1/22* (2006.01)
*B01D 15/38* (2006.01)
(52) U.S. Cl. ........... 530/413; 436/161; 210/198.2
(58) Field of Classification Search .......... None
See application file for complete search history.

(56) References Cited

U.S. PATENT DOCUMENTS

| 5,310,688 A | 5/1994 | Zale et al. | |
|---|---|---|---|
| 5,683,916 A * | 11/1997 | Goffe et al. | 436/535 |
| 2008/0124812 A1 | 5/2008 | Snyder et al. | |

OTHER PUBLICATIONS

Pikula et al. "Organic anion-transporting ATPase of rat liver. I. Purification, photoaffinity labeling, and regulation by phosphorylation," J. Biol. Chem. 1994, vol. 269, No. 44, pp. 27566-27573.*
A manual R-BIQPHARM AG, "RIDA Ochratoxin A column Immunoatffnity column for sample clean up prior to analysis of ochratoxin A," Nov. 14, 2003, pp. 1-19.*

* cited by examiner

*Primary Examiner* — Shafiqul Haq
*Assistant Examiner* — Galina Yakovleva
(74) *Attorney, Agent, or Firm* — Kilpatrick Townsend & Stockton LLP.; M. Henry Heines

(57) ABSTRACT

In an affinity-type purification, ligands dissociated from a packed bed that would otherwise leach into the solution containing the species being purified are captured by a second ligand that resides in a porous barrier downstream from the packed bed, the second ligand exhibiting an affinity-type interaction with the dissociated first ligand with sufficient specificity to avoid the undesired retention by the second ligand of species from the liquid sample or source liquid other than the species sought to be purified in the affinity column.

16 Claims, 1 Drawing Sheet

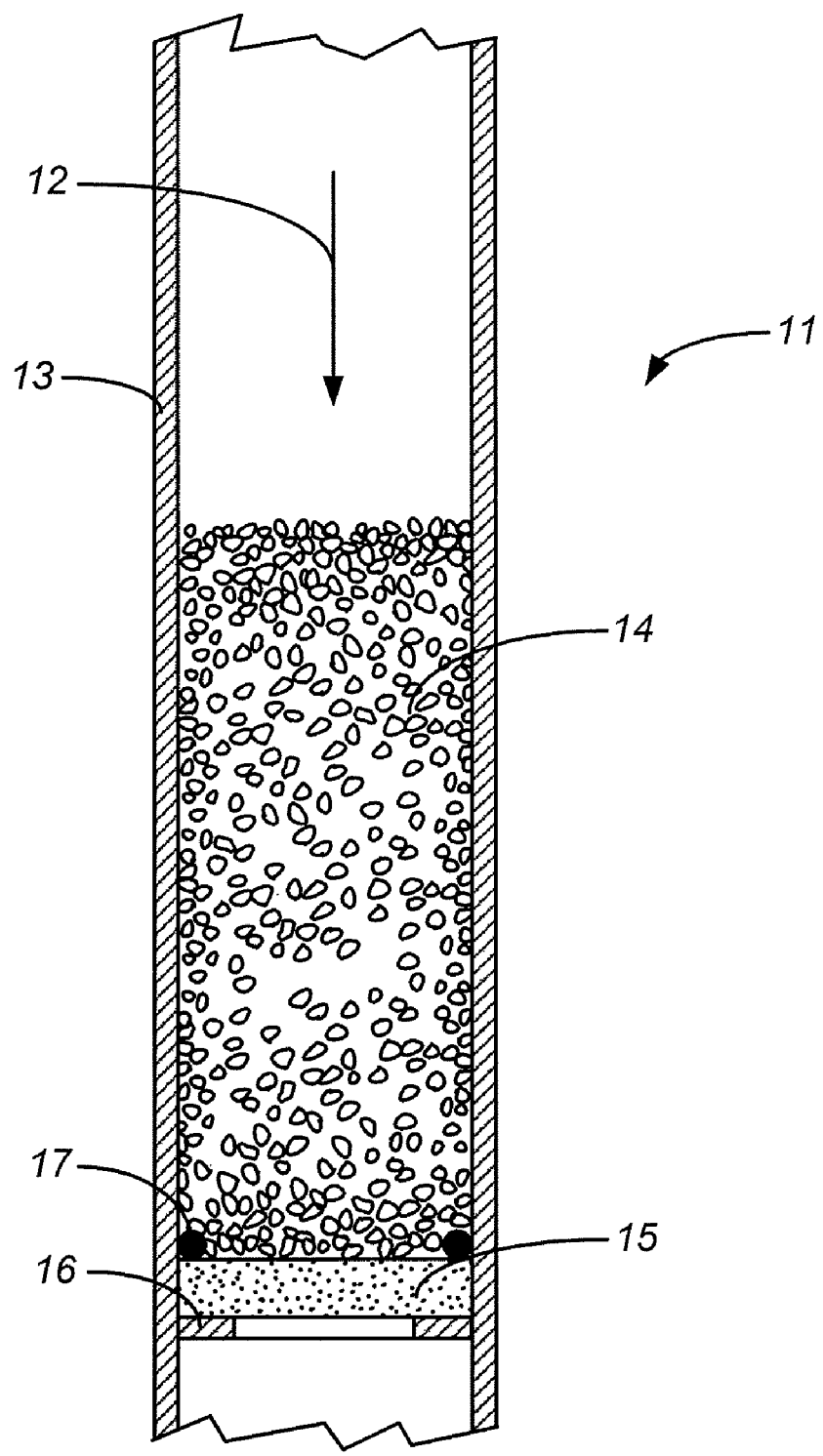
FIGURE

MULTI-MEDIA AFFINITY COLUMN TO PREVENT LEACHING OF LIGANDS

BACKGROUND OF THE INVENTION

1. Field of the Invention

This invention resides in the field of affinity chromatography, and addresses concerns arising from the labile character of ligands coupled to a support as the stationary phase.

2. Description of the Prior Art

Affinity chromatography is widely used for separating and detecting components in biological samples and for the isolation or purification of biological species or recombinant species from clinical samples, cell growth cultures, or any medium in which the species are produced or can be extracted. Affinity chromatography is commonly performed by passing a liquid medium containing the species of interest through a column or membrane to which a ligand is bound as a stationary phase, the ligand being one to which the species of interest binds by an affinity-type interaction. Affinity chromatography that is used for isolation and purification is also termed "affinity extraction," and the species-ligand interaction in this type of extraction is one that occurs with sufficient specificity to differentiate between the species of interest and other species in the source liquid. Affinity extraction techniques include immunoextraction in which the ligands are antibodies; protein-protein extractions using such ligands as wheat germ agglutinin, concanavalin A, protein A, and protein G; and interactions involving non-protein species such as heparin or nucleic acids. Once the species of interest is immobilized by the bound ligand as a result of the affinity interaction, ligand and its support are washed to remove unbound species and the bound species is then released from the ligand. Release is effected by an appropriate change in conditions such as a change in pH or the introduction of a detergent, chaotrope, salt, competitive binding species, or any agent that will overcome or lessen the binding affinity of the species to the ligand. The types of changes that will be effective in releasing the bound species in particular systems are well known in the art of affinity chromatography.

The ligand is typically a protein or other affinity-binding species that is coupled by covalent bonding to a solid support to form the stationary phase, the support often having been activated to facilitate the covalent bonding. Activation commonly involves the placement of a reactive group, one example of which is an epoxide group, on the support surface. The linkage between the ligand and the support is typically labile, however, leaving the ligand prone to dissociation from the support as the sample and other liquids pass through the medium. In addition to dissociation due to a simple shift in equilibrium, dissociation can also occur as the result of enzymatic or chemical degradation of the ligand itself. Proteases in the process stream can cause proteolysis of protein affinity ligands, for example, and endo- and exo-nucleases can cause cleavage of nucleic acid ligands. The amount of ligand that is leached as a result of this dissociation may be small compared to the amount of ligand remaining on the support, but even a small amount of leached ligand can seriously contaminate the otherwise purified species eluted from the medium. When a therapeutic agent that is either biologically derived or produced by recombinant chemistry is contaminated with a leached affinity ligand, the leached ligand can recombine with the agent and thereby impede the effectiveness of the agent, or bind to, or impede the functions of, other species or tissues in the patient's body, such as membranes, cell walls, or enzymes, causing harm. Concanavalin A, for example, is an affinity ligand that is used for purifying lysosomal enzyme preparations, but is known to leach from affinity columns and contaminate the enzyme preparations, particularly by activating T cells in the patient to whom the enzyme preparation is administered. To eliminate these types of contamination, the leached ligands must be removed, and this is typically performed by separations downstream of the affinity column or membrane. This adds cost and time to the preparation.

SUMMARY OF THE INVENTION

The present invention resides in an affinity column, and a process for its use, that prevent species purified in the medium from being contaminated with leached ligands from the column or leached segments of the ligands that have become dissociated during the passage of liquids through the column, and does so without the need for separations downstream of the affinity column. The column is a flow-through column that operates in the bind/elute mode and a porous barrier downstream of the packed bed which operates in a flow-through mode, both of which serve as supports for bound ligands. The ligand bound to the packed bed is the ligand that binds to the solute, i.e., the species to be extracted from the sample, and the ligand bound to the porous barrier is the ligand that binds selectively to molecules of the first (solute-binding) ligand, or segments of the first ligand, that become dissociated from the packed bed. Both ligands bind to their respective binding partners by an affinity-type interaction. Thus, while the solute-binding ligand is initially immobilized on the stationary phase by covalent binding, leached molecules of the ligand are captured by affinity binding in the same column. A single column therefore serves both to isolate the species of interest and to remove contaminants that would otherwise arise within the affinity medium itself.

Details regarding these and other features, advantages, and objects of the invention will be apparent from the description that follows.

BRIEF DESCRIPTION OF THE DRAWING

The FIGURE is a cross section of an example of an affinity column in accordance with the present invention.

DETAILED DESCRIPTION OF THE INVENTION AND PREFERRED EMBODIMENTS

The ligand (or ligands) that resides in the packed bed and that captures the species sought to be extracted in the practice of this invention are referred to herein as the "first ligand" to differentiate it from the "second ligand" which represents the ligand (or ligands) that captures leached molecules of the first ligand. The first ligand includes any of the wide variety of ligands that are used in affinity chromatography, and preferably those that are disclosed in the literature or used in clinical laboratories, research laboratories, or production facilities, as stationary phases for affinity extraction. First ligands can be protein ligands, polysaccharides, or other molecules that engage in affinity binding. Lectins are examples of ligands useful as the first ligand, effective for extracting certain types of carbohydrates, such as polysaccharides, glycoproteins, and glycolipids. Specific lectins include concavalin A, wheat germ agglutinin, jacalin, and lectins found in peas, peanuts, and soybeans. Protein A and protein G, useful in binding to the constant regions of many types of immunoglobulins, are further examples of ligands useful as the first ligand. A ligand demonstrating the binding behavior of both protein A and G is the recombinant protein known as protein A/G, which is also useful as the first ligand. In immunoextraction, as noted above, the first ligand is an antibody (including monoclonal antibodies) or an antibody fragment. Examples of species purified by immunoextraction using these ligands are anti-idiotypic antibodies, glucosaccharides, granulocyte colony-stimulating factor, human serum albumin, IgG, IgE, interferon, tumor necrosis factor, interleukins, recombinant Factor VIII, and transferrin. Still further examples of the first ligand are non-protein ligands. Examples of these are aptamers and heparin. Aptamers exhibit antibody-type interactions and are known for affinity-type binding to adenosine and for chiral separations, while heparin is useful for purifying certain lipoproteins.

The second ligand, which captures dissociated molecules of the first ligand to prevent these molecules from leaching into the product, is chosen for its affinity binding specificity toward the first ligand, and the choice will therefore be governed or dictated by the first ligand. Examples of species suitable for use as the second ligand thus include monoclonal antibodies, proteins, small peptides, aptamers, and organic species such as triazines and boronates. The second ligand is preferably one that does not bind other species in the liquid mixture that contains the species of interest, other than molecules of the first ligand that have become dissociated and would otherwise leach out of the medium.

The packed bed to which the first ligand is bound is a bed of any particulate material that can serve as a stationary phase support in affinity chromatography. Beads, fibers, and granules are examples. Beads, whether made of rigid solids or semi-solids such as gels, are preferred. The particle size is not critical to the invention and can vary widely. Best results in most cases will be obtained using beads of diameters ranging from about 20 microns to about 250 microns. The porous barrier can likewise be made of any material that can serve as a support for a solid phase in affinity chromatography, but one that can be formed into a disk or sheet that can span the entire cross section of the column. Examples are a frit, a film supported on a grid or frit, and a membrane. Membranes are preferred. The pore size can vary widely and is likewise not critical to the invention; the selection will depend on the other components of the system and the throughput rate and will be readily apparent to those of skill in the art. Best results in most cases will likely be achieved with pore sizes ranging from about 0.5 micron to about 20 microns. The thickness of the barrier will likewise be a matter of choice and routine experimentation if necessary. The lateral dimensions of the barrier and the manner in which the barrier is secured in the column are selected to prevent any bypass of fluid around the barrier. The barrier can thus be held in place by gaskets, o-rings, or similar conventional components.

The ligands can be coupled to their respective supports by conventional coupling chemistries, typically with the supports being activated or functionalized for coupling. Functionalization with epoxide groups is one example. Examples of the types of linkage are ether linkages, thiol linkages, amino linkages, carboxyl linkages, and aldehyde linkages. The relative amounts of first and second ligand can be selected on the basis of known or suspected dissociation rates of the first ligand, and may vary with the first ligand and the type of linkage joining the first ligand to the particles in the packed bed. These parameters are either known to those skilled in the art or readily determinable by routine experimentation.

The source liquid containing the solute of interest can be passed through an affinity column that meets the above description in the same manner that an affinity extraction column is used in the prior art. Flow of the source liquid through the column will be performed under conditions that will allow the solute to bind to the ligand on the packed bed. Such conditions are likewise known in the art, and involve such parameters as the pH, ionic strength, contact time, and the presence or absence of other components in the liquid phase. Once binding has occurred, the unbound species are washed from the column, using conventional washing media that will remove the unbound species from the packed bed without causing dissociation of the solute. Once the washing is complete, the bound solute is dissociated from the packed bed and collected by exposing the packed bed to the dissociation conditions most appropriate to the species involved. As noted above, the dissociation conditions may be a change in pH or the introduction of a detergent, a chaotrope, a salt, or competitive binding species. The result will be a solution of the solute that is purified relative to other solutes in the source liquid. The expression "purified relative to" is used herein to mean that while the concentration of the solute of interest as recovered from the affinity medium may be the same, greater than, or less than its concentration in the source solution, other solutes originally present in the source solution will be either significantly reduced in concentration, reduced to concentrations below the level of detection, or eliminated entirely.

An example of an affinity column in accordance with the present invention is shown in the attached FIGURE. The column 11 is a tubular column with a circular cross section, and the FIGURE is a cross section along a plane that includes the axis of the column. The direction of flow through the column is indicated by the arrow 12. The column consists of a cylindrical housing 13 with a packed bed 14 of beads. The solute-binding (first) ligand is covalently bonded to the surfaces of the beads. The beads rest above a liquid-permeable membrane 15 that serves the porous barrier. The ligand that binds the dissociated solute-binding ligand is covalently bonded to the membrane. The membrane 15 is supported by an internal ring or flange 16, and the periphery of the membrane is sealed against the wall of the housing by an o-ring 17.

The terms "a" or "an" as used in the appended claims are intended to mean "one or more." The term "comprise," and variations thereof such as "comprises" and "comprising," when preceding the recitation of a step or an element is intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly stated in this specification of the same word or phrase.

What is claimed is:

1. An affinity column for extracting a solute from a liquid sample, said column comprising:
   a flow-through tubular housing defining a flow direction therethrough;
   a packed bed of solid particulate support material with a first ligand immobilized thereon that binds selectively to said solute by affinity-type binding; and
   a porous barrier spanning said housing at a site downstream of said packed bed in said flow direction, said porous barrier having a second ligand immobilized thereon that binds selectively by affinity-type binding to molecules of said first ligand or to segments of said molecules upon release of said molecules or segments of said first ligand from said solid particulate support material.

2. The affinity column of claim 1 wherein said solid particulate support material are beads.

3. The affinity column of claim 1 wherein said porous barrier is a membrane.

4. The affinity column of claim 1 wherein said solid particulate support material are beads and said porous barrier is a membrane.

5. The affinity column of claim 1 wherein said first and second ligands are immobilized on said solid particulate support material and said porous barrier, respectively, by covalent binding.

6. The affinity column of claim 1 wherein said first ligand is a member selected from the group consisting of a lectin, heparin, protein A, and protein G.

7. The affinity column of claim 1 wherein said second ligand is a member selected from the group consisting of a monoclonal antibody, an aptamer, a triazine, and a boronate.

8. The affinity column of claim 1 wherein said first ligand is a member selected from the group consisting of a lectin, heparin, protein A, and protein G, and said second ligand is a member selected from the group consisting of a monoclonal antibody, an aptamer, a triazine, and a boronate.

9. A process for extracting a solute from a liquid sample, said process comprising:
(a) passing said liquid sample through the affinity column of claim 1, along said flow direction and under conditions causing said solute to bind to said first ligand;
(b) washing said packed bed while said solute is so bound by passing a wash solution through said affinity column; and
(c) dissociating said solute from said affinity medium in a purified form relative to other solutes in said liquid sample.

10. The process of claim 9 wherein said solid particular support material are beads.

11. The process of claim 9 wherein said porous barrier is a membrane.

12. The process of claim 9 wherein said solid particulate support material are beads and said porous barrier is a membrane.

13. The process of claim 9 wherein said first and second ligands are immobilized on said solid particulate support material and said porous barrier, respectively, by covalent binding.

14. The process of claim 9 wherein said first ligand is a member selected from the group consisting of a lectin, heparin, protein A, and protein G.

15. The process of claim 9 wherein said second ligand is a member selected from the group consisting of a monoclonal antibody, an aptamer, a triazine, and a boronate.

16. The process of claim 9 wherein said first ligand is a member selected from the group consisting of a lectin, heparin, protein A, and protein G, and said second ligand is a member selected from the group consisting of a monoclonal antibody, an aptamer, a triazine, and a boronate.

\* \* \* \* \*